US008754119B2

(12) United States Patent
Scheller et al.

(10) Patent No.: US 8,754,119 B2
(45) Date of Patent: *Jun. 17, 2014

(54) USE OF ROTIGOTINE FOR THE TREATMENT OF DEPRESSION

(75) Inventors: Dieter Scheller, Neuss (DE); Alexander Breidenbach, Weil am Rhein (DE); Norma Selve, Troisdorf (DE)

(73) Assignee: UCB Pharma GmbH, Monheim (DE)

( * ) Notice: Subject to any disclaimer, the term of this patent is extended or adjusted under 35 U.S.C. 154(b) by 747 days.

This patent is subject to a terminal disclaimer.

(21) Appl. No.: 10/565,699

(22) PCT Filed: Jul. 22, 2004

(86) PCT No.: PCT/EP2004/008168
§ 371 (c)(1),
(2), (4) Date: Jan. 25, 2006

(87) PCT Pub. No.: WO2005/009424
PCT Pub. Date: Feb. 3, 2005

(65) Prior Publication Data
US 2007/0093546 A1    Apr. 26, 2007

(30) Foreign Application Priority Data

Jul. 26, 2003 (DE) .................................. 103 34 188

(51) Int. Cl.
*A01N 43/06* (2006.01)
*A61K 31/38* (2006.01)
*C07D 333/12* (2006.01)
*C07D 333/20* (2006.01)
*A61K 31/135* (2006.01)
*A61K 31/381* (2006.01)

(52) U.S. Cl.
CPC .............. *A61K 31/381* (2013.01); *A61K 31/135* (2013.01)
USPC .............................. 514/438; 514/731; 549/74

(58) Field of Classification Search
USPC ...................... 514/438, 731; 549/74
See application file for complete search history.

(56) References Cited

U.S. PATENT DOCUMENTS

| 4,320,148 A | 3/1982 | DeMarinis | 424/330 |
|---|---|---|---|
| 4,410,519 A | 10/1983 | Seiler | 424/226 |
| 4,501,890 A * | 2/1985 | Nichols et al. | 514/267 |
| 4,542,135 A | 9/1985 | Kobel et al. | 514/250 |
| 4,556,676 A | 12/1985 | Welch et al. | 514/554 |
| 4,564,628 A | 1/1986 | Horn | 514/438 |
| 4,722,933 A | 2/1988 | Horn | 514/438 |
| 4,769,028 A * | 9/1988 | Hoffmann et al. | 424/443 |
| 4,824,860 A | 4/1989 | Owen | 514/418 |
| 4,863,951 A | 9/1989 | Peglion et al. | 514/422 |
| 4,863,970 A | 9/1989 | Patel et al. | 514/784 |
| 4,874,768 A | 10/1989 | Huth et al. | 514/288 |
| 4,885,308 A | 12/1989 | Horn | 514/438 |
| 4,996,226 A | 2/1991 | Horn | 514/438 |
| 5,071,875 A | 12/1991 | Horn | 514/613 |
| 5,151,446 A | 9/1992 | Horn et al. | 514/617 |
| 5,177,112 A | 1/1993 | Horn | 514/65 |
| 5,214,156 A | 5/1993 | Andersson et al. | 549/75 |
| 5,382,596 A | 1/1995 | Sleevi et al. | 514/459 |
| 5,462,947 A | 10/1995 | Svensson et al. | 514/317 |
| 5,486,611 A | 1/1996 | Lin et al. | 546/62 |
| 5,496,843 A | 3/1996 | Nagata et al. | 514/411 |
| 5,545,755 A | 8/1996 | Lin et al. | 564/428 |
| 5,614,518 A | 3/1997 | Leeson et al. | 514/234.5 |
| 5,633,376 A | 5/1997 | Thurkauf et al. | 544/360 |
| 5,656,286 A | 8/1997 | Miranda et al. | 424/449 |
| 5,658,955 A | 8/1997 | Hitzig | 514/654 |
| 5,663,167 A | 9/1997 | Pickar et al. | 514/225.8 |
| 5,681,956 A | 10/1997 | Thurkauf et al. | 544/295 |
| 5,807,855 A | 9/1998 | Bogeso et al. | 514/449 |
| 5,891,891 A | 4/1999 | Benincasa | 514/300 |
| 5,902,603 A | 5/1999 | Chen et al. | 424/449 |
| 5,906,830 A | 5/1999 | Farinas et al. | 424/448 |
| 6,001,861 A | 12/1999 | Oertel et al. | 514/367 |
| 6,010,877 A | 1/2000 | Sathe et al. | 435/69.1 |
| 6,024,976 A | 2/2000 | Miranda et al. | 424/449 |
| 6,107,318 A | 8/2000 | Pocchiari et al. | 514/366 |
| 6,221,627 B1 | 4/2001 | Sathe et al. | 435/69.1 |
| 6,255,329 B1 | 7/2001 | Maj | 514/367 |
| 6,300,365 B1 | 10/2001 | Holman | 514/418 |
| 6,331,636 B1 | 12/2001 | Romero et al. | 548/235 |
| 6,350,773 B1 * | 2/2002 | Marquis | 514/411 |
| 6,372,920 B1 | 4/2002 | Minaskanian et al. | 549/75 |
| 6,465,004 B1 | 10/2002 | Rossi-Montero et al. | 424/448 |

(Continued)

FOREIGN PATENT DOCUMENTS

| CA | 2532804 | 2/2005 |
|---|---|---|
| CA | 2532859 | 2/2005 |

(Continued)

OTHER PUBLICATIONS

Pkeiffer, Roland F. "Potential of Transdermal Drug Delivery in Parkinson's Disease", Drugs Aging, 2002, vol. 19, No. 8, pp. 561-570.*
Beaulieu et al. "N,N-disubstituted 2-aminotetralins are potent D-2 dopamine receptor agonists" European Journal of Pharmacology, Oct. 1984, vol. 105, issue 1-2, pp. 15-21, abstract provided (paper ordered).*
Belluzzi et al. "N-0923, a selective dopamine D2 receptor agonist, is efficacious in rat and monkey models of Parkinson's disease" Mov. Disord., Mar. 1994, vol. 9, No. 2, pp. 147-154, abstract provided (paper ordered).*
Muscat et al. "Antidepressant-like effects of dopamine agonists in an animal model of depression" Biological Psychiatry, May 1992, vol. 31, issue 9, pp. 937-946, abstract provided (paper ordered).*
Corrigan et al. "Comparison of Pramipexole, Fluoxetine, and Placebo in Patients with Major Depression" Depression and Anxiety, 2000, vol. 11, 58-65.*

(Continued)

*Primary Examiner* — Kendra D Carter
(74) *Attorney, Agent, or Firm* — Harness, Dickey & Pierce, P.L.C.

(57) ABSTRACT

The present invention relates to the use of rotigotine [(−)-5,6,7,8-tetrahydro-6-[propyl[2-(2-thienyl)ethyl]amino]-1-naphthol] and its prodrugs and pharmaceutically acceptable salts for producing a pharmaceutical agent for treating depression.

62 Claims, 3 Drawing Sheets

(56) References Cited

U.S. PATENT DOCUMENTS

| | | | |
|---|---|---|---|
| 6,884,434 B1 | 4/2005 | Muller et al. | 424/487 |
| 7,038,085 B2 | 5/2006 | Rariy et al. | 564/165 |
| 7,309,497 B2 | 12/2007 | Rimpler et al. | 424/422 |
| 7,413,747 B2 | 8/2008 | Mueller et al. | 424/449 |
| 2002/0177626 A1 | 11/2002 | Cook et al. | 514/570 |
| 2003/0026830 A1 | 2/2003 | Lauterbach et al. | 424/449 |
| 2003/0027793 A1* | 2/2003 | Lauterback et al. | 514/63 |
| 2003/0166709 A1 | 9/2003 | Rimpler et al. | 514/447 |
| 2003/0180332 A1* | 9/2003 | Rimpler et al. | 424/400 |
| 2003/0225002 A1 | 12/2003 | Livingstone | 514/23 |
| 2004/0034083 A1 | 2/2004 | Stephenson et al. | 514/406 |
| 2004/0048779 A1 | 3/2004 | Schollmayer et al. | 514/2 |
| 2004/0081683 A1 | 4/2004 | Schacht et al. | 424/449 |
| 2004/0116537 A1 | 6/2004 | Li et al. | 514/663 |
| 2004/0137045 A1 | 7/2004 | Breitenbach et al. | 424/449 |
| 2004/0209861 A1 | 10/2004 | Benavides et al. | 514/210.01 |
| 2005/0032843 A1 | 2/2005 | Pieper et al. | 514/338 |
| 2005/0032873 A1 | 2/2005 | Hatzenbuhler et al. | 514/414 |
| 2005/0033065 A1 | 2/2005 | Mueller et al. | 549/449 |
| 2005/0037983 A1* | 2/2005 | Dinan et al. | 514/28 |
| 2005/0038015 A1* | 2/2005 | Bronzova et al. | 514/220 |
| 2005/0079206 A1 | 4/2005 | Schacht et al. | 424/449 |
| 2005/0107397 A1 | 5/2005 | Galambos et al. | 514/255.03 |
| 2005/0175678 A1 | 8/2005 | Breitenbach | 424/448 |
| 2005/0182090 A1 | 8/2005 | Mierau et al. | 514/304 |
| 2005/0197385 A1 | 9/2005 | Scheller et al. | 514/438 |
| 2005/0260254 A1 | 11/2005 | Breitenbach et al. | 424/449 |
| 2005/0260577 A1 | 11/2005 | Double et al. | 435/6 |
| 2006/0216336 A1 | 9/2006 | Wolff | 424/448 |
| 2006/0263419 A1 | 11/2006 | Wolff | 424/448 |
| 2007/0072917 A1 | 3/2007 | Scheller et al. | 514/357 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |
| 2010/0311806 A1 | 12/2010 | Wolff et al. | 514/438 |
| 2011/0104281 A1 | 5/2011 | Beyreuther et al. | 424/486 |
| 2011/0165247 A1 | 7/2011 | Breitenbach | 424/486 |
| 2012/0101146 A1 | 4/2012 | Bouwstra et al. | 514/438 |
| 2012/0215185 A1 | 8/2012 | Schacht et al. | 604/290 |
| 2012/0322845 A1 | 12/2012 | Wolff et al. | 514/438 |

FOREIGN PATENT DOCUMENTS

| | | | |
|---|---|---|---|
| CA | 2547820 | 6/2005 | |
| CA | 2568850 | 2/2006 | |
| DE | 4325855 | 2/1995 | |
| EP | 0 334 538 | 9/1989 | |
| WO | WO 93/00313 | 1/1993 | |
| WO | WO 93/16073 | 8/1993 | |
| WO | WO 94/07468 | 4/1994 | A61K 9/14 |
| WO | WO 94/21244 | 9/1994 | |
| WO | WO 94/26703 | 11/1994 | |
| WO | WO 95/18603 | 7/1995 | |
| WO | WO 96/31210 | 10/1996 | |
| WO | WO 97/09971 | 3/1997 | |
| WO | WO 97/29735 | 8/1997 | |
| WO | WO 99/15210 | 4/1999 | |
| WO | WO 99/49852 | 10/1999 | |
| WO | WO 00/02053 | 6/2000 | |
| WO | WO 00/35954 | 6/2000 | |
| WO | WO 00/37426 | 6/2000 | |
| WO | WO 00/37438 | 6/2000 | |
| WO | WO 01/38321 | 5/2001 | |
| WO | WO 01/39756 | 6/2001 | |
| WO | WO 01/62249 | 8/2001 | |
| WO | WO 01/81343 | 11/2001 | |
| WO | WO 02/15903 | 2/2002 | |
| WO | WO 02/38646 | 5/2002 | |
| WO | WO 02/089777 | 11/2002 | |
| WO | WO 02/089778 | 11/2002 | |
| WO | WO 02/098367 | 12/2002 | |
| WO | WO 03/029233 | 4/2003 | |
| WO | WO 03/088958 | 10/2003 | |
| WO | WO 2004/039320 | 5/2004 | |
| WO | WO 2004/058247 | 7/2004 | |
| WO | WO 2005/009424 | 2/2005 | A61K 31/135 |
| WO | WO 2005/063238 | 7/2005 | |
| WO | WO 2005/070428 | 8/2005 | |
| WO | WO 2006/015737 | 2/2006 | |
| WO | WO 2006/050976 | 3/2006 | |
| WO | WO 2006/039532 | 4/2006 | |
| WO | WO 2006/069030 | 6/2006 | |

OTHER PUBLICATIONS

Arnt et al. "differential involvement of dopamine D-1 and D=2 receptors in the circling behaviour induced by apomorphine, SK & F 38393, pergolide and Ly 171555 in 6-hydroxydopamine-lesioned rats" Psychopharmacology, 1985, vol. 85, pp. 346-352.*

Fisch, et al. (2003) "Fluoxetine versus pacebo in advanced cancer outpatients: A double-blinded trial of the Hoosier oncology group." J Clin Oncol. 21(10): 1937-1943.

Hrdlička (2002) "Combination of clozapine and maprotiline in refacatory psychotic depression." Eur Psychiatry 17:484.

Joffe, et al. (1997) "Co-administration of fluoxetine and sumatriptan: the Canadian experience." Acta Psychiatr Scand 95(6):551-552 (PubMed Abstract Only).

Kupfer (1999) "Pathophysiology and management of insomnia during depression." Ann Clin Psychiatry 11(4): 267-276.

Lehmann (1989) "The dose-effect relationship of 0.5, 1.0 and 1.5 mg Fluspirilene on anxious patients." Neuropsychobiology 21(4): 197-204.

Links between depression and migraine (2003) (http://www.biomedicine.org/medicine-news/Links-between-Depression-and-Migraine-2005-1/).

McAllister-Williams (http://www.netdoctor.co.uk/diseases/depression/classification_000001.htm) p. 1-7.

Preskorn, et al. Antidepressants: Past, Present and Future, p. 1-4.

Ranjan, et al. (1996) "Acute and long-term effectiveness of Clozapine in treatment-resistant psychotic depression." Biol Psychiatry 40:253-258.

Sherman (2001) "Augmentation strategy aids treatment-resistant depression. (Dopamine Agonist).(pramipexole for mental depression)." Clinical Psychiatry News p. 1-2.

Sobow (2001) "Tianeptine versus fluoxetine in the treatment of depression complicating Alszheimer's disease." Int J Geriatr Psychiatry 16:1108-1109.

Timmerman, et al. (1989) "The potential antipsychotic activity of the partial dopamine receptor agonist (+)N-0437." Eur J Pharmacol 181:253-260.

Van der Weide, et al. (1988) "The enantiomers of the D-2 dopamine receptor agonist N-0437 discriminate between pre- and postsynaptic dopamine receptors." Eur J Pharmacol 146:319-326.

Antidepressant (http://en.wikipedia.org/wiki/Antidepressant) p. 1-27.

Zimmerman, et al. (2003) "Generalized anxiety disorder in patients with major depression: is DMS-IV's hierarchy correct?" Am J Psychiatry 160:504-512.

Office Action, dated Apr. 7, 2009 issued in U.S. Appl. No. 10/565,713.

Office Action, dated Dec. 7, 2009 issued in U.S. Appl. No. 10/565,713.

Bertaine-Anglade, V., et al. (2006) "Antidepressant properties of Rotigotine in experimental models of depression," *European Journal of Pharmacology*. 548: 106-114.

Goetz, G., et al. (2003) "The Unified Parkinson's Disease Rating Scale (UPDRS): Status and Recommendations," *Movement Disorders*. 18 (7): 738-750.

Rotigotine (Transdermal Route) (2007) http://www.mayoclinic.com/health/drug-information/DR602471/DSECTION=proper-use. p. 1-8.

Scheller, D., et al. (2009) "The in vitro receptor profile of Rotigotine: a new agent for the treatment of Parkinson's disease," *Naunyn-Schmiedeberg's Arch. Pharmacol*. 379: 73-86.

(56) References Cited

OTHER PUBLICATIONS

Wang, W., et al. (2007) "Effects of Apomorphine on the Expression of Learned Helplessness Behavior," *Chinese Journal of Physiology*. 50 (2): 63-68.
Office Action, dated Oct. 16, 2008 issued in U.S. Appl. No. 10/587,637.
Office Action, dated Sep. 2, 2009 issued in U.S. Appl. No. 10/587,637.
Office Action, dated Jun. 7, 2010 issued in U.S. Appl. No. 10/587,637.
Office Action, dated Nov. 1, 2002 issued in U.S. Appl. No. 09/647,290.
Office Action, dated Sep. 13, 2007 issued in U.S. Appl. No. 10/936,620.
Office Action, dated May 1, 2008 issued in U.S. Appl. No. 10/936,620.
Office Action, dated Jan. 26, 2009 issued in U.S. Appl. No. 10/936,620.
Office Action, dated Nov. 6, 2009 issued in U.S. Appl. No. 10/936,620.
Office Action, dated Oct. 8, 2010 issued in U.S. Appl. No. 10/936,620.
ADIS R&D Profile (2003) Drugs R&D 4(6), Abstract SR 58611A SR 58611; 380-382.
Dryer et al. (1980) Federation Proceedings 39(3), page Abstract 3051.
http://en.wikipedia.org/wiki/Apomorphine (printed Jun. 6, 2011).
Welner et al. (1989) Synapse 4(4), 347-352.
Office Action dated Apr. 19, 2011 issued in U.S. Appl. No. 10/565,713.
Human Medicines Evaluation Unit (1998), "Note for guidance on clinical investigation of medicinal products in the treatment of parkinson's disease", *The European Agency for the Evaluation of Medicinal Products*, CPMP/EWP/563-95.
Reichmann, H., et al. (2002), Pramipexol bei der Parkinson-Krankheit, Springer-verlag, 8(73): 744-750.—Partial Translation Only.
Http://en.wikipedia.org/wiki/Dysthymia (printed Sep. 21, 2012).
Dr Voderholzer, U., "What distinguishes a depressive mood from a depression?"—Full Translation.
Lehrbuch der Psychiatrie, H. Hinterhuber und W.W. Fleischhacker, 1997, Georg Thieme Verlag, S. 44.—Partial Translation.
Baghai, T., et al. (2006), "Drug treatment of depression in the 2000s: An overview of achievements in the last 10 years and future possibilities", *The World Journal of Biological Psychiatry*, 7(4): 198-222.
Full Prescribing Information for Neupro. Last revised Apr. 2012.
Burn, D. (2002), "Beyond the iron mask: towards better recognition and treatment of depression associated with parkinson's disease", *Movement Disorders*, 17(3): 445-454.
*Movement Disorders*, (2002), "Treatment of depression in idiopathic parkinson's disease", 17(4): S112-S119.
Chung, T.H., et al. (2003), "Systematic review of antidepressant therapies in parkinson's disease", *Parkinsonism and Related Disorders*, 10: 59-65.
http://www.who.int/classifications/icd/en/ (printed Sep. 21, 2012).
http://apps.who.int/classifications/apps/icd/icd10online2003/navi/htm (printed Sep. 21, 2012).
European Opposition for European Application No. 04 741 204.4 dated Sep. 4, 2012—Full Translation.
Allain (2000), "Depression in Parkinson's Disease", *BMJ*, 320: 1287-1288.
Gotham, A., et al., (1986), "Depression in Parkinson's Disease: a quantitative and qualitative analysis", *Journal of Neurology, Neurosurgery, and Psychiatry*, 49: 381-389.
Office Action, dated Mar. 23, 2007 in U.S. Appl. No. 10/713,424.
Office Action, dated Sep. 14, 2007 in U.S. Appl. No. 10/713,424.
Office Action, dated Apr. 24, 2008 in U.S. Appl. No. 10/517,157.
Office Action, dated Aug. 6, 2008 in U.S. Appl. No. 10/517,157.
Office Action, dated Sep. 10, 2008 in U.S. Appl. No. 10/429,283.
Office Action, dated Nov. 12, 2008 in U.S. Appl. No. 10/623,864.
Office Action, dated Dec. 10, 2008 in U.S. Appl. No. 10/565,713.
Office Action, dated Mar. 6, 2009 in U.S. Appl. No. 10/517,157.
Office Action, dated Mar. 30, 2009 in U.S. Appl. No. 10/429,283.
Office Action, dated Apr. 20, 2009 in U.S. Appl. No. 10/593,964.
Office Action, dated Jun. 24, 2009 in U.S. Appl. No. 10/623,864.
Office Action, dated Aug. 5, 2009 in U.S. Appl. No. 10/593,964.
Office Action, dated Nov. 24, 2009 in U.S. Appl. No. 10/517,157.
Office Action, dated Dec. 21, 2009 in U.S. Appl. No. 11/239,701.
Office Action, dated Dec. 23, 2009 in U.S. Appl. No. 10/429,283.
Office Action, dated Jan. 6, 2010 in U.S. Appl. No. 10/623,864.
Office Action, dated Aug. 16, 2010 in U.S. Appl. No. 11/239,701.
Office Action, dated Aug. 31, 2010 in U.S. Appl. No. 10/623,864.
Office Action, dated Oct. 1, 2010 in U.S. Appl. No. 10/429,283.
Office Action, dated May 4, 2011 in U.S. Appl. No. 10/429,283.
Office Action, dated May 12, 2011 in U.S. Appl. No. 10/623,864.
Office Action, dated Sep. 22, 2011 in U.S. Appl. No. 10/565,713.
Office Action, dated Feb. 3, 2012 in U.S. Appl. No. 10/429,283.
Office Action, dated Jun. 11, 2012 in U.S. Appl. No. 12/744,989.
Office Action, dated Jul. 12, 2012 in U.S. Appl. No. 13/457,848.
Office Action dated Sep. 10 2013 issued in U.S. Appl. No. 10/565,713.
AADAC (2004) Beyond the ABCs: Amphetamines (from www.aadac.com), 5pp.
Arnt (1984) Pol. J. Pharmacol. Pharm. 36, 221-230.
Balsara et al. (1982) Ind. J. Physiol. Pharmac. 26(3), 183-195.
Barfknecht et al. (1973) J. Medicinal Chemistry 16(7), 804-805.
Bartoszyk (1998) Life Sciences 62(7), 649-663.
Becker et al. (2002) J. Neurol. 249(Suppl. 3), III/40-III/48.
Bell (1977) Br. J. Pharm. 61, 291-295.
Bijak (1988) Eur. J. Pharmacol. 149, 41-47.
Bischoff et al. (1986) Satellite Symp. IUPHAR 9th Int. Congr. Pharmacol. "Dopaminergic Systems and their Regulation", 397-398.
Borsini (1988) Eur. J. Pharmacol. 148, 301-307.
Bunney et al. (1982) Pharmacopsychiatry 15, 111-115.
Caliendo et al. (2005) Current Medicinal Chemistry 12, 171-173.
Camicioli (2002) Drugs of Today 38(10), 677-686.
Carp et al. (1982) Brain Research 242, 247-254.
Chandler et al. (1990) Neuroscience 38(2), 437-445.
Chaudhuri (2002) Eur. J. Neurol. 9(3), 40-43.
Chiodo et al. (1980) Eur. J. Pharmacol. 64, 203-204.
Christie et al. (1982) Brit. J. Psychiatry 140, 268-273.
Collado-Seidel et al. (1999) CNS Drugs Jul. 12(1), 9-20.
Corsini et al. (1981) Biological Psychiatry, 742-745.
Dawson et al. (2002) Nature Neuroscience Supplement 5, 1058-1061.
De Boer et al. (1988) Neuropharmacology 27(4), 399-408.
De Ceballos et al. (1985) Eur. J. Pharmacology 116, 257-262.
Deakin (2002) Internatl. Clinical Psychopharm. 17(Suppl. 1), S13-S24.
Den Daas et al. (1990) (Naunyn-Schmiedeberg's Arch. Pharmacol. 342, 655.
Den Daas et al. (1991) J. Pharm. Pharmacol. 43, 11.
DeNinno et al. (2001) J. Organic Chemistry 66, 6988-6993.
Diggory et al. (1984) Eur. J. Pharmacol. 105, 257-263.
Doggett (1973) Neuropharmacology 12, 213-220.
Domino et al. (1993) J. Pharmacol. Exp. Ther. 264(1), 221-225.
Duterte-Boucher et al. (1988) Eur. J. Pharmacol. 154, 185-190.
Errico et al. (2001) Neuroscience 102(2), 361-367.
Estrada-Camerena et al. (2006) Neuropsychopharmacology 31, 247-255.
Faedda et al. (1989) Biochemical Pharmacology 38(3), 473-480.
Fajardo et al. (2003) International Immunopharm. 3, 1345-1352.
Foley et al. (2004) J. Neural Transmission 111, 1375-1446.
Friedman et al. (2004) Parkinsonism and Related Disorders 10, S27-S35.
Gerlach et al. (2003) J. Neural Transm. 65(Suppl.), 167-183.
Goodwin et al. (1987) Psychopharmacology 91, 500-505.
Gorman (1999) Psychiatry 60(Suppl), 17.
Graeff et al. (1971) Arch. Int. Pharmcodyn. 193, 134-148.
Green et al. (1983) Br. J. Pharmacol. 80, 377-385.
Grippo et al. (2005) Psychopharmacology 179, 769-780.
Guttman (2003) Can. Med. Assoc. J. 168(3), 293-301.

(56) References Cited

OTHER PUBLICATIONS

Gyure et al. (1985) Proc. 4th Congress Hungary Pharmacol. Soc. Budapest vol. 2, 309-312.
Haddjeri et al. (1999) Biol. Psychiatry 45, 1163-1169.
Happe (2004) CNS Drugs 18(1), 27-36.
Hauser et al. (2004) Neurol. Clin. 22, S149-S166.
Henderson (2003) J. Neurol. Neurosurg. Psychiatry 74, 956-958.
Hobson (2003) Can. J. Neurol. Sci. 30(Suppl. 1) S2-S9.
Holcomb et al. (1982) Eur. J. Pharmacol. 82, 173-178.
Holman (2004) Arthritis & Rheumatism 50(Suppl. 9), S698, Abstr. 1870.
Holman (2004) J. Musculoskeletal Pain 12(1), 69-74.
Holman (2005) Arthritis & Rheumatism 52(8), 2495-2505.
Hornykiewicz (2002) Encyclopedia of Life Sciences vol. 13, 695-704.
Hundemer et al. (2001) Sleep 24( Abstr. Suppl.), A17, Abstr. 027.N.
Jackson (1989) Naunyn-Schmiedeberg's Arch. Pharmacol. 340, 355-365.
Jimmerson et al. (1976) J. Pharm. Pharmacol. 28, 845-846.
Johnson et al. (1970) Proc. Western Pharmacol. Soc. 13, 87-92.
Johnson et al. (1970) Life Science 9(1), 471-476.
Johnston et al. (2004) Current Opinion Invest. Drugs 5(7), 720-726.
Joyce (2001) Pharmacol. Ther. 90, 231-259.
Kamata (1984) Life Sciences 34, 2419-2427.
Keller (1980) Adv. Biochem. Psychopharmacol. 24, 175-179.
Kelly et al. (1997) Pharmacol. Ther. 74(3), 299-316.
Khaitan (1994) Psychopharmacol. 113, 529-542.
Kim et al. (1993) J. Pharmaceutical Sciences 82(4), 355-361.
Klimek et al. (1987) Eur. J. Pharmacol. 139(2) 163-169.
Klimek et al. (1989) J. Pharm. Pharmacol. 41(8), 455-558.
Knott et al (1990) in Bowery et al., eds., "$GABA_B$ Receptors in Mammalian Function", pp. 336-346.
Koe et al. (2006) Abstr. 231st ACS Nat. Meeting, Abstr. MEDI-185.
Koide et al. (1981) Life Sciences 28(10), 1139-1145.
Kostowski (1992) Pharmacology & Toxicology 71(1), 24-30.
Lee et al. (1982) Psychiatry Research 7, 111-119.
Levien (2005) Advances in Pharmacy 3(1), 62-92.
LeWitt (2007) Neurology 68(16), 1262-1267.
Linazasoro (2004) Movement Disorders 19(7), 743-754.
Littlejohn (2006) Current Pharm. Design 12, 3-9.
Liu et al. (1993) J. Med. Chemistry 36, 4221-4229.
Menon et al. (1972) Eur. J. Pharmacol. 19, 43-51.
Metman (2001) Clinical Neuropharmacol 24(3), 163-169.
Modigh et al. (1984) in Lerer et al., eds. "ECT: Basic Mechanisms": John Libbey, pp. 18-27.
Mulroney et al. (1994) J. Pharmacol. Exp. Ther. 288(2), 862-867.
Murray (1997) Lancet 349, 1498.
Newman-Tancredi (2002) J. Pharmacol. Exp. Ther. 303(2), 805-813.
Nowak et al. (1985) J. Neural Transmission 64, 227-238.
Nurse et al. (1984) Neurochemical Research 9(9), 1231-1238.
Ong et al. (1988) J. Pharm. Pharmacol. 40, 746-747.
Ono et al. (1984) Neuropharmacol. 23(6), 637-642.
Ono et al. (1989) J. Pharmacobiol-Dyn. 12, 384-391.
Ostow (2002) American J. Psychiatry 159(2), 320-321.
Page (2002) J. Pharmacol. Exp. Ther. 302(3), 1220-1227.
Park (1972) Current Therapeutic Research 14(2), 65-70.
Pascual (1992) Annals of Neurology 32(5), 703-707.
Pessoa-Mahna et al. (2003) Mini Reviews in Medicinal Chemistry 3(2), 77-93.
Piercey et al. (1990) Eur. J. Pharmacol. 182, 219-226.
Porsolt (1979) Biomedicine 30, 139-140.
Pradhan et al. (1989) Drug Develop. Research 18, 113.118.
Rammsayer (1997) Int. J. Neurosci. 91, 45-55.
Reith (1986) Pharmcol. Biochem. & Behavior 24, 305-307.
Robertson (1981) Neuropharmacology 20, 1335-1336.
Sarges et al. (1973) J. Medicinal Chemistry 16(9), 1003-1011.
Schatzberg (2002) Human Psychophamiacol. 17, S17-S22.
Schelkunov (1980) J. Neurol. Transmission 47, 307-312.
Scriabine (2003) CNS Drug Reviews 9(4), 389-395.
Serra et al. (1981) Eur. J. Pharmacol. 72(1), 131-135.
Sharma (2002) Neurol. Clin, N. Am. 20, 759-778.
Shepperson et al. (1982) Eur. J. Pharmacol. 81, 627-635.
Sherman (1982) Pharm. Biochemistry & Behavior 16, 449.
Shiro et al. (1996) Psychiatry & Clinical Neurosciences 50, 141-146.
Skuza et al. (1989) Pol. J. Pharmacol. Pharm. 41, 421-429.
Sonesson (1995) J. Med. Chem. 38(8), 1319-1329.
Stiasny-Kolster et al. (2005) "Rotigotine in the Treatment of Moderate to Severe Idiopathis Restless Legs Syndrome—a Double-Blind Placebo-Controlled Multi-Center Dose-Finding Study", presented at EFNS Conf.
Stockmeier et al. (1992) Neuropharmacol. 31(11), 1089-1094.
Stockmeier et al. (1997) Neuropsychopharmacology 16(2), 162-173.
Stockmeier (1998) J. Neuroscience 18(18), 7394-7401.
Sumiyoshi et al. (1997) Neuropsychopharmacol. 16, 183-190.
Timmerman et al. (1990) Eur. J. Pharmacol. 181(3), 253-260.
Tuite (2003) Expert Opinion Investig. Drugs 12(8), 1335-1352.
Van Gaalen et al. (2002) Genes, Brain & Behavior 1, 174-177.
Van Riezen et al. (1977) Br. J. Pharmacol. 60(4), 521.
Vance (1983) Research Comm. Chem. Pathology & Pharmacology 40(2), 345-348.
Westenberg (1999) J. Clin. Psychiatry 60 (Suppl 17).
Wikstrom (1992) Progress in Medical Chemistry 29, 185-216.
Willner et al. (1988) in "Progress in Catecholamine Research, Part C, Clinical Aspects", pp. 275-279.
Zhdanova (2004) Expert Opinion Pharmacotherapy 5(7), 1573-1579.
Mutschler Arzneimittelwirkungen. Lehrbuch der Pharmakologie und Toxikologie. 9. Auflage S. 173-175.(2008)—Partial Translation.
Mutschler Arzneimittelwirkungen. Lehrbuch der Pharmakologie und Toxikologie 7. Auflage. S. 261-262. (1997)—Partial Translation.

* cited by examiner

USE OF ROTIGOTINE FOR THE TREATMENT OF DEPRESSION

CROSS-REFERENCE TO RELATED APPLICATIONS

This application is a U.S. national stage filing under 35 U.S.C. §371 of International Application No. PCT/EP2004/008168 filed on Jul. 22, 2004, which claims priority of German Application No. DE 103 34 188.9 filed on Jul. 26, 2003. This application contains subject matter that is related to a concurrently filed U.S. Application by the same applicants titled "Substituted 2-aminotetralin for the treatment of depression" (Ser. No. 10/565,713). The disclosure of each of the applications identified in this paragraph is incorporated herein by reference in its entirety.

According to estimates of the WHO, depression will be the second most common cause of disability caused by illness by 2020 (Murray, Lancet 349 (1997) 1498). The efficiency of current pharmacological treatments is limited for various reasons, for example because of late onset of effect, side effects or lack of effectiveness of the pharmaceutical agents. There is a great need for new, innovative antidepressants because of the frequency and duration of this illness and the tendency to relapse.

Until now, amine reuptake inhibitors or monoamine oxidase inhibitors have primarily been used as antidepressants (Goodman & Gilman's *The Pharmacological Basis of Therapeutics,* 9th Edition). Very recently, the use of active ingredients which influence both serotonergic (5HT1) and adrenergic receptors (a2) has been discussed as a very promising therapy concept (Westenberg, *J. Clin. Psychiatry* 60, Suppl. 17, 1999, 4; Schatzberg, *Human Psychopharmacology* 17, 2002, p. 17). One example of an active ingredient with a dual action principle of this type is mirtazapine (Gorman, *J. Clin. Psychiatry* 60, Suppl. 17, 1999, 9).

A fast onset of action and superior effectiveness in comparison to conventional antidepressants is expected from active ingredients with a dual action principle, as the high selectivity of the active ingredients and the favourable side effect profile connected therewith allows a rapid adjustment of the patient to the individual maintenance dose (Deakin, Int. Clin. Psychopharmacology 17, Suppl. 1, 2002, p. 13).

The dopamine agonists pramipexol and ropinirol were recently attributed an antidepressive effectiveness and this effect was demonstrated in clinical studies (Ostow, M., *Am. J. Psychiatry,* 2002 February; 159(2):320-1). However, it is still unclear here as to what contribution the dopamine agonism and what contribution possible other effects of the dopamine agonists investigated make as these also influence other neurotransmitter systems substance-specifically.

It has now surprisingly been found that the rotigotine described as a dopamine agonist (Metman, *Clinical Neuropharmacol.* 24, 2001, 163) binds both to a2 receptors and to the 5HT1A receptor. While rotigotine acts antagonistically on a2 receptors, it exhibits agonistic activity on 5HT1A receptors.

With this profile, in particular with respect to the surprising agonistic 5HT1A activity, rotigotine [(−)-5,6,7,8-tetrahydro-6-[propyl[2-(2-thienyl)ethyl]amino]-1-naphthol] is a candidate for use as an antidepressant.

The suitability of rotigotine as an antidepressant was demonstrated in three different, validated animal models.

The "forced swim test" is an animal model, in which depressive episodes are triggered by acute stress. In this case, rats are forced to swim in a limited space. After initial attempts to save themselves, in which the animals grasp the hopelessness, they lapse into immobility. On repetition of the experiment, the animals remain immobile from the beginning of the experiment. In the event of pre-treatment with antidepressants, the period of immobility is shortened during the repetition experiment; the animals generally start searching and escape movements directly after transfer into the water basin (Porsolt, *Biomedicine* 30, 1979, 139). Rotigotine leads to a significantly shortened period of immobility.

In the "learned helplessness test", rats are repeatedly subjected to uncontrollable stress. This brings about an impaired learning ability in the animals in a later situation (for example after 48 h), in which they could escape the stress again. After sub-chronic, but not acute administration of antidepressants, the learning ability normalises again and the animals learn to escape the (announced) stress (in time), (Sherman, *Pharmacology Biochemistry & Behavior* 16, 1982, 449). After several days of administration of rotigotine depot suspension (Embodiment 2) the animals exhibited improved learning behaviour at low concentrations; nevertheless the higher doses also increased the activity of the animals under non-test conditions.

In a further animal model (Embodiment 3) an investigation was made as to whether the antidepressive effects of rotigotine can be distinguished from a general motor stimulation. In this case, rotigotine was administered to rats, whose olfactory bulb had been removed on both sides. The removal of the olfactory bulb leads in the untreated control group to an adaptive hyperactivity. It is known from the literature that chronically administered antidepressants lead to a reduction in movement activity of the animals in this model, while stimulants further increase the motor activity (van Riezen H et al., Br. J. Pharmacol. 60(4), 1977, 521; Kelly J P et al., Pharmacol. Ther. 74(3), 1997, 299). Therefore, it is possible to discriminate between antidepressive and non-specific stimulatory effects of an active ingredient with this model. It has now been shown that rotigotine exhibits a specifically antidepressive effect in low doses that approximately corresponds to the effect of the antidepressant imipramine and which leads to virtually complete suppression of the bulbectomy-induced locomotor hyperactivity. In higher rotigotine concentrations, on the other hand, the stimulatory dopamine-agonistic effect predominates.

It could thus be clearly shown that subcutaneously applied rotigotine surprisingly has a significant antidepressive effect in all three tests.

Figure 1:
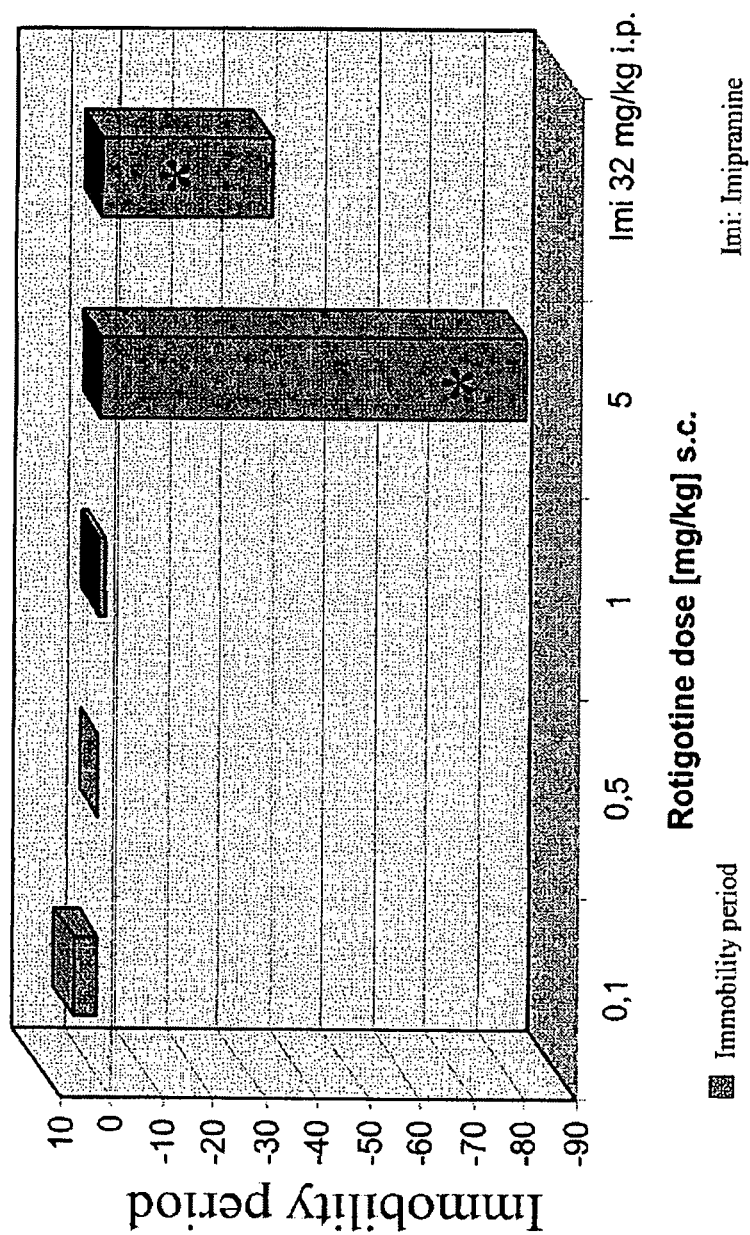
FIG. 1 shows that rotigotine leads to a clear reduction in the immobility period in the "forced swim test".
Figure 2:
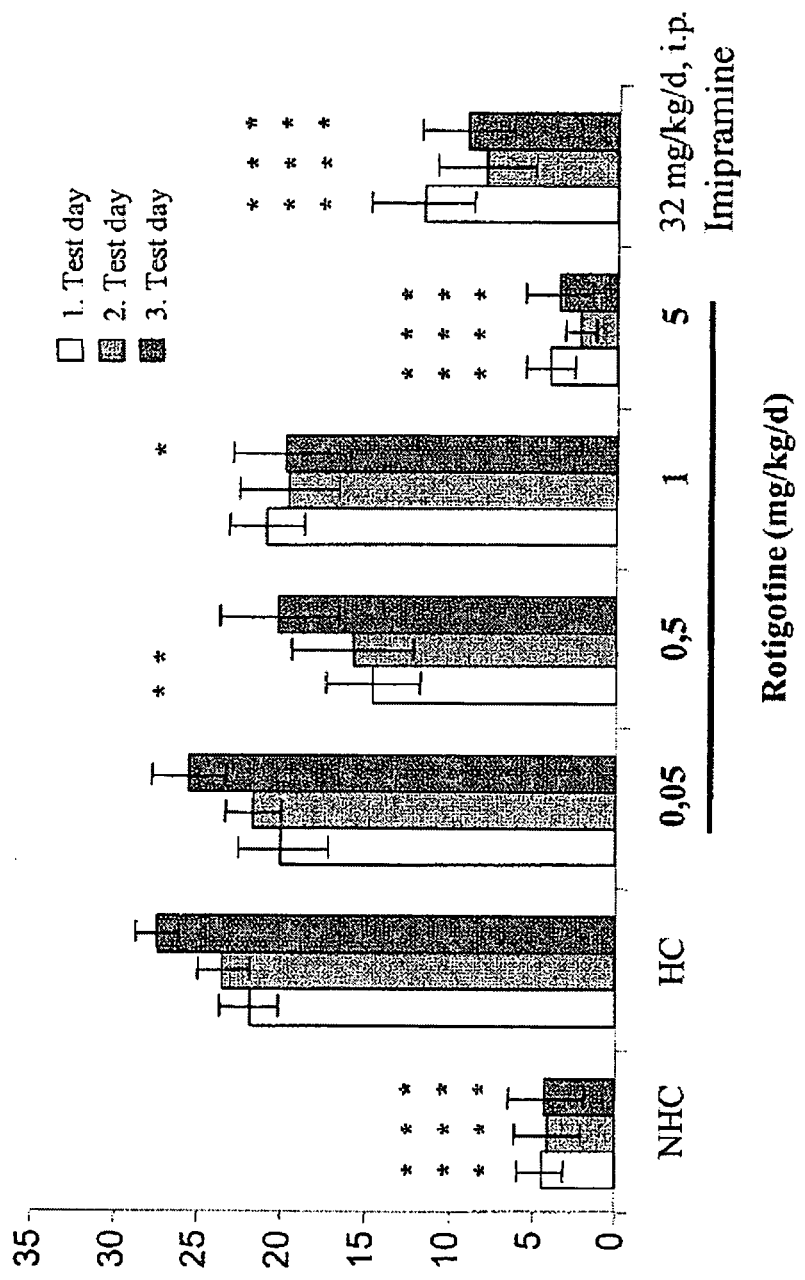
FIG. 2 shows that animals treated with rotigotine depot suspension (Embodiment 2) in the "learned helplessness test" exhibit a normalised learning behaviour (NHC), depending on the dose, compared to the control group (HC) treated only with excipient.
Figure 3:
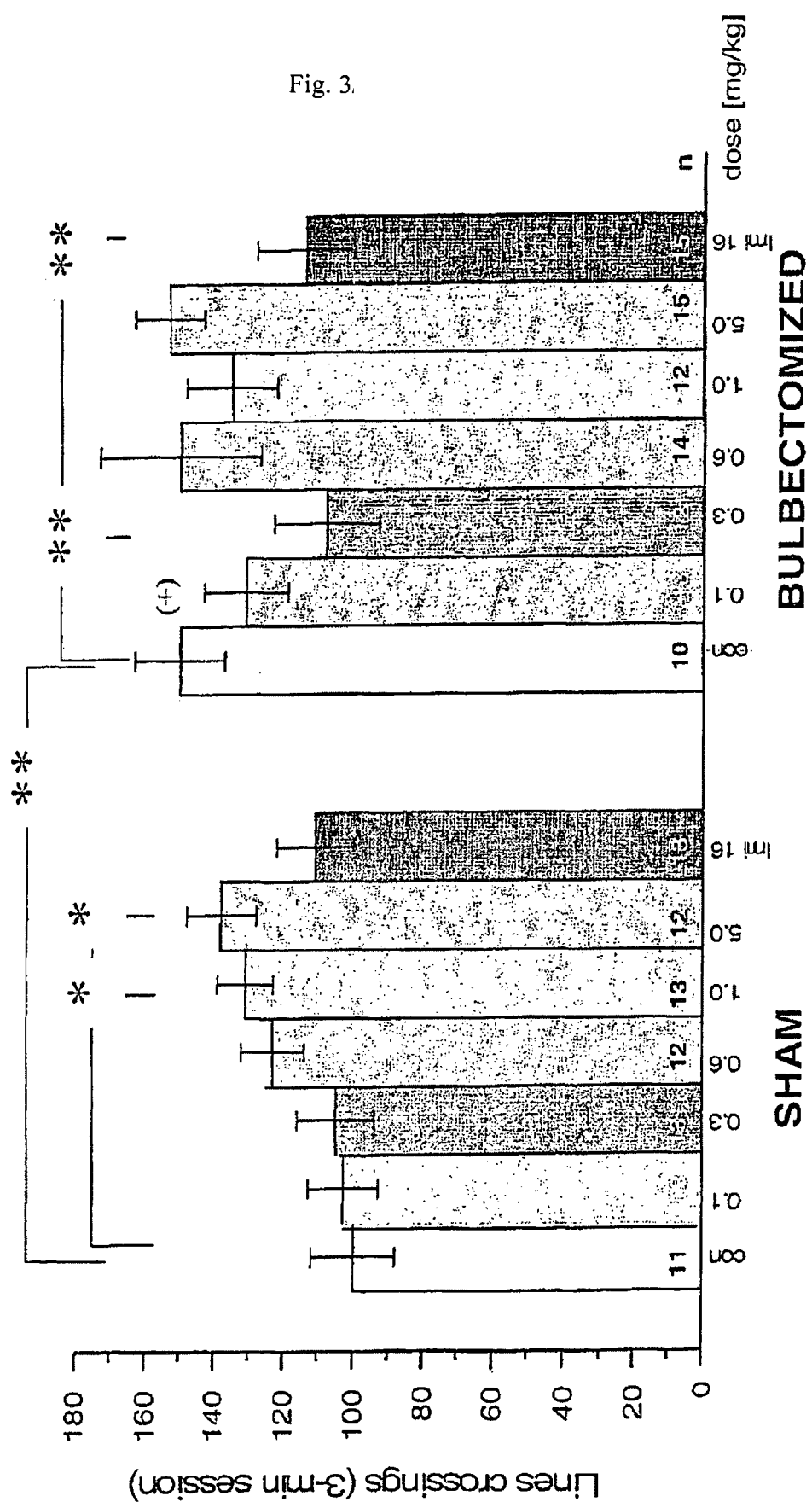
FIG. 3 shows that rotigotine in low doses in bulbectomised rats (Embodiment 3) significantly reduces the motor hyperactivity and therefore develops a clear antidepressive effect. In higher doses, on the other hand, a non-specific activation of the locomotor activity dominates and occurs both in bulbectomised animals and also in control animals.

The conclusion emerges from these preclinical data that new effective pharmaceutical agents can be made available for treating depression with rotigotine, its biologically active metabolites and the corresponding prodrugs and salts.

A subject of the invention is therefore the use of rotigotine, its prodrugs and salts for producing a pharmaceutical agent for treating depression, and a method for treating depression in a mammal, comprising administering to the mammal a therapeutically effective amount of rotigotine, or a prodrug thereof, or a physiologically acceptable salt thereof. The term "treating" in this patent application comprises both the treatment of existing depression and the preventative treatment (prophylaxis) of depression, for example of recurring depressive phases.

Depressive disorders are divided for better understanding and to achieve an optimum individual therapy into subforms, with the transitions of the various subforms often being blurred. Depression is classified—traditionally—according to its presumed causes or—latterly—according to its symptoms (see in this regard ICD-10 "International Statistical Classification of Diseases and Related Health Problems" of the WHO).

In this application, the term "depression" is taken to mean both the various traditional subforms of depression mentioned below and the disorders subsumed under the term "affective disorders" in ICD-10, which accompany depressive episodes, in particular depressive episodes, recurrent depressive disorders, depressive phases in bipolar affective disorders and anxiety disorders, adaptation disorders and organic brain diseases which accompany depressive symptoms in each case. Corresponding disorders are listed, for example in the ICD-10 classifications (Version 2.0, November 2000) F31, F32, F33, F41, F43, F45 and F06.

In the conventional division of depression according to causes, 4 main classes are generally distinguished:

I. Endogenous Depression

No easily discernible external causes can be identified as triggers of the depression in endogenous depression. Triggers are probably disorders of the neurotransmitter system of the brain. The phase-like course where the depressive episodes can occur repeatedly is typical of endogenous depression. Endogenous depression is generally divided into unipolar depression ("major depression"), in which only depressive phases occur bipolar depression ("manic-depressive disorders"), in which depressive episodes alternate with manic phases.

II. Somatogenic Depression

Physical-organic disorders are the cause of this depression. Generally, somatogenic depression is divided into organic depression, based on an illness or injury to the brain. Such illnesses or injuries, which are often accompanied by a changed brain metabolism are, for example, brain tumours, Parkinson's disease, migraines, epilepsy, brain paralysis, arteriosclerosis of the brain, brain traumas, meningitis, stroke and dementias, such as, for example, Alzheimer's disease;

symptomatic depression which often occurs as a result of or as an accompanying symptom of an illness which only indirectly influences the brain function. This may be, for example a circulatory illness, hypothyroidism, or another hormone disorder, infectious disease, cancer or liver disease;

pharmacogenic depression, for example in the case of alcohol, medication or drug misuse.

III. Psychogenic Depression

This is often an overreaction to one or more traumatic experiences. It is frequently subdivided into exhaustion-depression, neurotic depression and reactive depression on the basis of current conflicts or events.

IV. Depression in Particular Circumstances

Examples are postpartum depression, age depression, childhood depression, seasonal depression and puberty depression.

Rotigotine and its prodrugs and salts are basically suitable for administering to a mammal for treating the various, above-mentioned forms of depression or for treating affective disorders, in particular depressive episodes, recurring depressive disorders and depressive phases in bipolar affective disorders, according to ICD-10.

According to the invention, rotigotine is preferably used for treating depressive episodes and serious recurring depressive disorders such as occur, for example in endogenous, unipolar depression ("major depression").

Metabolic disorders of the brain cells, i.e. noradrenaline or lack of serotonin and/or a genetic predisposition are regarded as causes of endogenous, unipolar depression.

Designated under the term "major depression" in this application is, in particular, a disorder such as described in the American diagnosis manual "The Diagnostic and Statistic Manual of Mental Disorders—4th Edition" (American Psychiatric Association, 1994; "DSM IV").

Rotigotine [(−)-5,6,7,8-tetrahydro-6-[propyl[2-(2-thienyl) ethyl]amino]-1-naphthol] and its prodrugs and salts are also especially suitable for treating depressive episodes in manic-depressive patients.

These depressive phases in bipolar disorders are subsumed in this patent application under the term "depression".

Rotigotine is also preferably used for treating "organic" depression, as described above. Organic depression occurs frequently, for example, in Parkinson's disease, or in cerebrovascular diseases and in dementia disorders.

In the treatment of depression, which occurs as a result of Parkinson's disease, the conclusion which is relevant for clinical practice emerges from the present invention that the conventional co-medication of antidepressants and anti-Parkinson's agents is not required when the depressive Parkinson's patients are put on rotigotine.

A subject of the invention is therefore the use of rotigotine, its metabolites, prodrugs and salts, for producing a pharmaceutical agent for the treatment of depression associated with Parkinson's disease; and a method for treating depression associated with Parkinson's disease in a mammal, comprising administering to the mammal a therapeutically effective amount of rotigotine, or a metabolite, a prodrug or a physiologically acceptable salt thereof, it being possible optionally to dispense with co-medication with other antidepressants.

Another subject of the invention is the use of rotigotine, its metabolites, prodrugs and salts, in each case alone or in combination with other antidepressants, for treating organic depression, which is not associated with Parkinson's disease; and a method for treating organic depression not associated with Parkinson's disease in a mammal, comprising administering to the mammal a therapeutically effective amount of rotigotine, or a metabolite, prodrug or salt thereof, alone or in combination with another antidepressant. Examples of such organic depression are depression in conjunction with brain tumours, migraines, epilepsy, brain paralysis, brain arteriosclerosis, brain traumas, meningitis, stroke, dementia, Alzheimer's disease or the Parkinson Plus Syndrome.

A further subject of the invention is a method for treating depression in a mammal, in particular endogenous, unipolar depression ("major depression"), a depressive phase of a bipolar disorder, Parkinson's-associated depression or an organic depression which is independent of Parkinson's disease by administering a therapeutically effective quantity of rotigotine, a metabolite, prodrugs or salt to said mammal, in particular to a human.

"Prodrugs" of rotigotine are taken in this patent application to mean, in particular compounds which are cleaved, converted or metabolised in the human body, in particular in the plasma or when passing through skin or mucous membrane in an effective quantity to form rotigotine.

Examples of prodrugs are esters, in particular alkanoyl esters and particularly preferably alkanoyl esters with up to 6 carbon atoms. Other examples of prodrugs are carbamates, carbonates, ketals, acetals, phosphates, phosphonates, sulphates and sulphonates.

The production of prodrugs by the reaction of rotigotine with correspondingly reactive precursors such as acid chlorides, acid anhydrides, carbamoyl chlorides, sulphonyl chlorides etc. is known to the person skilled in the art in the area of medical chemistry and can be found in the relevant technical literature.

Examples of literature references are Bundgaard: *Design of Prodrugs*, Elsevier, Amsterdam, 1985; Higuchi and Stella: *Pro-drugs as Novel Drug Delivery Systems*, in American Chemical Society, Washington D.C., 1975; Sloan: *Pro-drugs—Topical and Ocular Drug Delivery*, Ed: M. Dekker, 1992; Roche: *Design of Biopharmaceutical Properties through Prodrugs and Analogs*, Washington, D.C., 1977.

The basic suitability of a rotigotine derivative as a prodrug can be determined in that the respective compound is incubated under defined conditions with an enzyme mixture, a cell preparation, a cell homogenate or an enzyme-containing cell fraction and the rotigotine developing is measured. A suitable enzyme mixture is, for example, contained in the S9-liver preparation from Gentest, Woburn, Mass., USA. To measure prodrugs which can be cleaved especially rapidly, the prodrug to be tested can also be incubated in plasma, for example plasma from human blood. The optimum hydrolysis speed of the prodrug depends on the objective. Prodrugs which can be cleaved rapidly may be suitable, for example for rapid flooding, for example in the case of nasal administration. Prodrugs which can be cleaved more slowly may be suitable, for example for retardation, for example in the case of transdermal, parenteral or oral administration.

Various prodrugs of the racemate of rotigotine (N-0437) are described, for example, in Den Haas et al., *Naunyn-Schmiedebery's Arch. Pharmacol.* 342, 1990, 655 and Den Haas et al., *J. Pharm. Pharmacol.* 43, 1991, 11.

In vivo, a prodrug should release so much rotigotine that a therapeutically effective steady-state concentration of rotigotine is obtained in the plasma. Generally regarded as therapeutically effective concentrations here are rotigotine concentrations between 0.05 and 20 ng/ml, preferably between 0.1 and 10 ng/ml and particularly preferably between 0.2 and 5 ng/ml plasma.

For the specific treatment of depression, however, lower rotigotine plasma levels may optionally be adequate, for example those under 2 ng/ml, for example between 0.05 and 1 ng/ml plasma or between 0.1 and 0.5 ng/ml plasma.

Rotigotine is the S-(−)-enantiomer of 5,6,7,8-tetrahydro-6-[propyl[2-(2-thienyl)ethyl]amino]-1-naphthol. This means that the proportion of (R)-enantiomers in the pharmaceutical agent is small according to the invention. The (R)-enantiomer is preferably present in a proportion of <10 mol %, particularly preferably in a proportion of <2 mol % and quite particularly preferably at a mol proportion of <1%, based on the total quantity of rotigotine in the antidepressant.

Rotigotine and its prodrugs can be present in the pharmaceutical agent as free bases or in the form of physiologically acceptable salts, for example in the form of hydrochloride.

"Physiologically acceptable salts" include non-toxic addition salts of a base, in particular a compound of a formula (I) in the form of the free base, with organic or inorganic acids, for example with HCl.

There are many methods of application for administering rotigotine and its prodrugs which the person skilled in the art can select and adapt depending on the need, state and age of the patient, required dosage and desired application interval.

A preferred type of administration of rotigotine is transdermal administration. The administration form may in principle be selected from, for example an ointment, paste, spray, film, plaster or an iontophoretic device.

Rotigotine is preferably applied, in this case, in plaster form to the skin of the patient, the active ingredient preferably being present in a matrix made of adhesive polymer, for example a self-adhesive adhesive polysiloxane (Embodiment 1). Examples of suitable transdermal formulations are to be found in WO 99/49852, WO 02/89777 and WO 02/89778. A form of administration of this type allows a substantially constant plasma level to be adjusted and therefore a constant dopaminergic stimulation over the entire application interval (WO 02/89778; Metman, *Clinical Neuropharmacol.* 24, 2001, 163).

If, on the other hand, an antidepressant in the form of a subcutaneous or intramuscular depot form is desired, the rotigotine may be suspended, for example as a salt crystal, for example as a crystalline hydrochloride in a hydrophobic anhydrous medium and injected, as described in WO 02/15903, or else administered in the form of microcapsules, microparticles or implants based on biodegradable polymers, such as described in WO 02/38646, for example.

Other conceivable forms of administration of rotigotine and its prodrugs are transmucosal formulations, for example sublingual sprays, nasal or rectal formulations or aerosols for pulmonary administration.

Suitable dosages of rotigotine are between 0.1 and about 50 mg/day, with daily doses preferably between 0.2 and 40 mg and in particular between 0.4 and 20 mg/day being administered. Particularly preferred dosages of rotigotine are above 0.5 mg/day, wherein for rotigotine applications, which do not require simultaneous treatment of Parkinson's disease motor disorders, such dosage forms are quite particularly selected in which the antidepressive effect of rotigotine is marked, but in which the non-specific stimulatory effect of rotigotine is as small as possible. Such dosages are, in general below 10 mg/day, for example below 7.5 mg or below 5, 4, 3, 2 or below 1 mg/day and in particular between 0.5 and 5 mg/day.

In the case of Parkinson's disease, on the other hand, a dosage of sometimes above 5 mg/day may be required for simultaneous therapy of the motor disorders. Corresponding dosages are, for example dependent on the age and condition of the patient, degree of severity of the illness etc., sometimes significantly above 1 mg/day, for example over 5, 6, 8, 9, 10 or even between 10 and 50 mg/day, for example between 10 and 25 mg/day.

Depending on the selected type of application, the desired daily dose may be controlled by the formulation design. For example, the daily dose of transdermally administered rotigotine can be adjusted by means of the adjustment of a corresponding flux rate per unit of area and/or by variation of the plaster size. In this case, the dosage may take place in a creeping fashion, in other words the treatment may optionally start with low dosages which are then increased to the maintenance dose.

A subject of the invention is therefore a dosage form, for example a plaster or an injectable deposit formulation which releases the appropriate required quantity of rotigotine for therapy of the depression, for example between 0.5 and 10 mg/day or between 0.5 and 5 mg/day, as described above.

It is clear to the person skilled in the art that the dosage interval may vary depending on the applied quantity, the type of application and the daily requirement of the patient. Thus a transdermal application form may be conceived, for example for a once daily, once every three days or once every seven days administration, while a subcutaneous or intramuscular depot may make possible injections, for example in a one-week, two-week or four-week rhythm.

Rotigotine and its prodrugs can be used as monotherapeutic agents for treating depression. In one embodiment of the invention, however, other active ingredients may be present, apart from rotigotine, in the antidepressive therapeutic agent form.

Examples of this are other antidepressants which directly or indirectly influence the serotonin or noradrenaline metabolism.

Examples of this are
  selective serotonin reuptake inhibitors, such as sertraline, citalopram, paroxetine or fluoxetine
  mixed serotonin and noradrenaline reuptake inhibitors such as venlaxafine, milnacipram, mirtazapine and tricyclic antidepressanats such as amitryptiline and imipramine
  selective noradrenaline reuptake inhibitors such as reboxetine
  monoaminoxidase inhibitors such as tranylcypramine or clorgyline
  alpha2-receptors and/or serotonin receptor-modulators such as mirtazapine or nefazodone.

Other examples of antidepressants are adenosine antagonists, such as for example, ST 1535, Sigma-opioid receptor ligands, NK antagonists such as GW 597599, saredudant or aprepitant, melatonin agonists or modulators of the hypothalamus-hypophysis-adrenal axis.

Depending on the cause and the symptoms of the depression, a combination preparation may also contain an additional antipsychotic, sedative, anxiolytic or migraine agent, or an active ingredient which develops one or more effects selected from an antidepressive, antipsychotic, sedative, anxiolytic or anti-migraine effect.

In the process the compound of Formula I or II and the additional antidepressant, antipsychotic, sedative, anxiolytic or migraine agent may be present in the same pharmaceutical formulation, for example a combination tablet, or else in different application units, for example in the form of two separate tablets. Depending on need, the two active ingredients may be administered simultaneously or temporally separately.

In a combination preparation, a sequential administration can be achieved, for example, in that an administration form, for example an oral tablet, has two different layers with a different release profile for the various pharmaceutically active ingredients. It is clear to the person skilled in the art that, in the context of the present invention, various forms of administration and application patterns are conceivable, which are all the subject of the invention.

Examples of antipsychotics are promethazine, fluphenazine, perphenazine, levomepromazine, thioridazine, perazine, promazine, chlorprothixene, zuclopenthixol, prothipendyl, flupentixol, zotepine, benperidol, pipamperon, melperon, haloperidol, bromperidol, sulpiride, clozapine, pimozide, risperidone, quetiapine, amisulpride, olanzapine.

Examples of sedatives are diphenhydramine, doxylamine succinate, nitrazepam, midazolam, lormetazepam, flunitrazepam, flurazepam, oxazepam, bromazepam, triazolam, brotizolam, temazepam, chloral hydrate, zopiclone, zolpidem, tryptophan, zaleplon.

Examples of anxiolytics are fluspirilene, thioridazine, oxazepam, alprazolam, bromazepam, lorazepam, prazepam, diazepam, clobazam, medazepam, chlordiazepoxide, dipotassium chlorazepate, nordazepam, meprobamate, buspirone, kavain, hydroxyzine.

Examples of migraine agents are almotriptan, zolmitriptan, acetylsalicylic acid, ergotamine, dihydroergotamine, methysergide, iprazochrome, ibuprofen, sumatriptan, rizatriptan, naratriptan, paracetamol.

EMBODIMENTS

Embodiment 1

Rotigotine Plaster 1.8 g rotigotine (free base) are dissolved in 2.4 g ethanol and added to 0.4 g collidone 90F (dissolved in 1 g ethanol). This mixture is added to a 74% solution of silicone polymers (8.9 g BioPSA 7-4201+8.9 g BIO-PSA 7-4301 [Dow Corning]) in heptane. After the addition of 2.65 g petrol ether, the mixture is stirred for 1 hour at 700 rpm in order to obtain a homogeneous dispersion. After lamination on polyester it is dried at 50° C. The plaster weight was finally 50 g/cm2.

Embodiment 2

Rotigotine Depot Suspensions (a) 1411.2 g Miglyol 812 was weighed into a Duran flask. 14.4 g Imwitor 312 were added to the Miglyol and then heated for 30 minutes to 80° C. whilst stirring. The clear solution was cooled to room temperature and filtered.

(b) 1188 g of the solution produced under (a) were transferred into a glass laboratory reactor, 12 g rotigotine were added and homogenised for 10 minutes under nitrogen with an Ultraturrax at 10,000 rpm. The suspension was decanted into brown glass bottles with the Ultraturrax running (2,000 rpm).

Embodiment 3

The bulbectomy study was carried out on Sprague-Dawley rats. A group, which had seemingly been operated on, served as a control group and was operated on without the olfactory bulb being removed. 14 days after the operation, the rats were treated with excipients, rotigotine depot suspension (every second day) or imipramine. On test days, the rats were taken onto a test field and left to themselves for 3 minutes. The locomotor activities of the animals were measured here with the aid of the number of lines crossed.

The invention claimed is:

1. A method for treating depression in a mammal, comprising administering a therapeutically effective quantity of rotigotine or a metabolite, prodrug or physiologically acceptable salt thereof, to said mammal.

2. The method of claim 1, wherein the mammal is human.

3. The method of claim 2, wherein the depression is an endogenous depression.

4. The method of claim 3, wherein the endogenous depression is a unipolar depression or a depressive episode of a manic-depressive disorder.

5. The method of claim 2, wherein the rotigotine is administered parenterally, transdermally or mucosally.

6. The method of claim 2, wherein the rotigotine is administered in a dosage of 0.5 to about 50 mg per day.

7. The method of claim 2, wherein the rotigotine is administered in a dosage of 0.5 to 10 mg per day.

8. The method of claim 2, wherein the rotigotine is administered in a dosage of 0.5 to 5 mg per day.

9. The method of claim 1, wherein the rotigotine is administered as a prodrug thereof.

10. The method of claim 9, wherein the prodrug is an ester, carbamate, carbonate, ketal, acetate, phosphate, phosphonate, sulfate or sulfonate.

11. The method of claim 1, wherein the rotigotine is administered transdermally as rotigotine free base or hydrochloride salt.

12. The method of claim 11, wherein the rotigotine is formulated as an ointment, paste, spray, film, plaster or iontophoretic device for transdermal administration.

13. The method of claim 11, wherein the rotigotine is formulated as a plaster having the rotigotine in a matrix comprising an adhesive polymer.

14. The method of claim 11, wherein a substantially constant plasma level of rotigotine is established.

15. The method of claim 1, further comprising administering to the mammal one or more antidepressants.

16. The method of claim 1, wherein the rotigotine is administered in monotherapy.

17. The method of claim 1, wherein the quantity of rotigotine is effective for alleviation of symptoms of Parkinson's disease and for treatment of depression.

18. The method of claim 17, wherein the rotigotine is administered in monotherapy.

19. The method of claim 2, wherein the depression is a somatogenic depression.

20. The method of claim 19, wherein the somatogenic depression is an organic depression not associated with Parkinson's disease.

21. The method of claim 19, wherein the somatogenic depression is an organic depression associated with Parkinson's disease.

22. The method of claim 21, wherein co-medication with another antidepressant is absent.

23. The method of claim 20, wherein the organic depression is associated with brain tumor, migraine, epilepsy, brain paralysis, arteriosclerosis of the brain, brain trauma, meningitis, stroke, Parkinson Plus syndrome, dementia and/or cerebrovascular disease.

24. The method of claim 20, wherein the organic depression is associated with Alzheimer's disease.

25. The method of claim 19, wherein the somatogenic depression is a symptomatic depression.

26. The method of claim 25, wherein the symptomatic depression is associated with circulatory illness, hypothyroidism, hormone disorder, infectious disease, cancer and/or liver disease.

27. The method of claim 19 wherein the somatogenic depression is a pharmacogenic depression.

28. The method of claim 27, wherein the pharmacogenic depression is associated with alcohol, medication and/or drug misuse.

29. The method of claim 2, wherein the depression is a psychogenic depression.

30. The method of claim 29, wherein the psychogenic depression comprises at least one of exhaustion depression, neurotic depression and reactive depression as a result of current conflicts or events.

31. The method of claim 2, wherein the depression occurs in particular circumstances, comprising at least one of postpartum depression, old-age depression, childhood depression, seasonal depression and pubertal depression.

32. The method of claim 1, wherein the depression is associated with an affective disorder.

33. The method of claim 32, wherein the affective disorder comprises a recurrent depressive disorder and/or depressive phases in bipolar affective disorder.

34. The method of claim 2, wherein the depression manifests as depressive symptoms accompanying at least one anxiety disorder, adjustment disorder and/or organic brain disease.

35. The method of claim 2, wherein the rotigotine is administered in a dosage of 0.1 to about 50 mg per day.

36. The method of claim 2, wherein the rotigotine is administered in a dosage of 0.2 to 40 mg per day.

37. The method of claim 2, wherein the rotigotine is administered in a dosage of 0.4 to 20 mg per day.

38. The method of claim 2, wherein the rotigotine or metabolite, prodrug or salt thereof is administered in an amount effective to obtain a plasma rotigotine concentration of 0.05 to 20 ng/ml.

39. The method of claim 2, wherein the rotigotine or metabolite, prodrug or salt thereof is administered in an amount effective to obtain a plasma rotigotine concentration of 0.1 to 10 ng/ml.

40. The method of claim 2, wherein the rotigotine or metabolite, prodrug or salt thereof is administered in an amount effective to obtain a plasma rotigotine concentration of 0.2 to 5 ng/ml.

41. The method of claim 2, wherein the rotigotine or metabolite, prodrug or salt thereof is administered in an amount effective to obtain a plasma rotigotine concentration of 0.1 to 0.5 ng/ml.

42. The method of claim 9, wherein the prodrug is administered in an amount effective to obtain a plasma rotigotine concentration of 0.05 to 20 ng/ml.

43. The method of claim 42, wherein the prodrug is administered in an amount effective to obtain a plasma rotigotine concentration of 0.1 to 10 ng/ml.

44. The method of claim 42, wherein the prodrug is administered in an amount effective to obtain a plasma rotigotine concentration of 0.2 to 5 ng/ml.

45. The method of claim 42, wherein the prodrug is administered in an amount effective to obtain a plasma rotigotine concentration of 0.1 to 0.5 ng/ml.

46. The method of claim 14, wherein the rotigotine is administered in an amount effective to obtain a plasma rotigotine concentration of 0.05 to 20 ng/ml.

47. The method of claim 14, wherein the rotigotine is administered in an amount effective to obtain a plasma rotigotine concentration of 0.1 to 10 ng/ml.

48. The method of claim 14, wherein the rotigotine is administered in an amount effective to obtain a plasma rotigotine concentration of 0.2 to 5 ng/ml.

49. The method of claim 14, wherein the rotigotine is administered in an amount effective to obtain a plasma rotigotine concentration of 0.1 to 0.5 ng/ml.

50. The method of claim 15, wherein the one or more antidepressants comprise one or more serotonin reuptake inhibitors, mixed serotonin and noradrenalin reuptake inhibitors, selective noradrenaline reuptake inhibitors, monoamine oxidase inhibitors, alpha2 receptor modulators, serotonin receptor modulators, adenosine antagonists, sigma-opioid receptor ligands, NK antagonists, melatonin antagonists and/or modulators of the hypothalamus-hypophysis-adrenal axis.

51. The method of claim 50, wherein the one or more anti-depressants comprise at least one of sertaline, citalopram, partoxetine, fluoxetine, venlaxafine, milnacipram, mirtazapine, amitryptiline, imipramine, reboxetine, tranylcypramine, clorgyline, and/or nefazodone.

52. The method of claim 1, further comprising administering to the mammal one or more antipsychotics.

53. The method of claim 52, wherein the one or more antipsychotics comprise at least one of promethazine, fluphenazine, perphenazine, levomepromazine, thioridazine, perazine, promazine, chlorprothixene, zuclopenthixol, prothipendyl, flupentixol, zotepine, benperidol, pipamperon, melperon, haloperidol, bromperidol, sulpiride, clozapine, pimozide, risperidone, quetiapine, amisulpride and/or olanzapine.

54. The method of claim 1, further comprising administering to the mammal one or more sedatives.

55. The method of claim 54, wherein the one or more sedatives comprise at least one of diphenhydramine, doxylamine succinate, nitrazepam, midazolam, lormetazepam, flunitrazepam, flurazepam, oxazepam, bromazepam, triazolam, brotizolam, temazepam, chloral hydrate, zopiclone, zolpidem, tryptophan and/or zaleplon.

56. The method of claim 1, further comprising administering to the mammal one or more anxiolytics.

57. The method of claim 56, wherein the one or more anxiolytics comprise at least one of fluspirilene, thioridazine, oxazepam, alprazolam, bromazepam, lorazepam, prazepam, diazepam, clobazam, medazepam, chlordiazepoxide, dipotassium chlorazepate, nordazepam, meprobamate, buspirone, kavain and/or hydroxyzine.

58. The method of claim 1, further comprising administering to the mammal one or more anti-migraine agents.

59. The method of claim 58, wherein the one or more anti-migraine agents comprise at least one of almotriptan, zolmitriptan, acetylsalicylic acid, ergotamine, dihydroergotamine, methysergide, iprazochrome, ibuprofen, sumatriptan, rizatriptan, naratriptan and/or paracetamol.

60. The method of claim 1, further comprising administering to the mammal at least one additional active ingredient comprising one or more antidepressants, antipsychotics, sedatives, anxiolytics and/or anti-migraine agents, wherein the rotigotine or metabolite, prodrug or salt thereof and the at least one additional active ingredient are provided in separate dosage forms for administration by the same or different routes at the same or different times.

61. The method of claim 1, further comprising administering to the mammal at least one additional active ingredient comprising one or more antidepressants, antipsychotics, sedatives, anxiolytics and/or anti-migraine agents, wherein the rotigotine or metabolite, prodrug or salt thereof and the at least one additional active ingredient are administered in a single dosage form.

62. A method for treating endogenous depression in a mammal, comprising administering a therapeutically effective quantity of rotigotine or a metabolite, prodrug or physiologically acceptable salt thereof, to said mammal.

* * * * *

UNITED STATES PATENT AND TRADEMARK OFFICE
CERTIFICATE OF CORRECTION

| | | |
|---|---|---|
| PATENT NO. | : 8,754,119 B2 | Page 1 of 1 |
| APPLICATION NO. | : 10/565699 | |
| DATED | : June 17, 2014 | |
| INVENTOR(S) | : Dieter Scheller et al. | |

It is certified that error appears in the above-identified patent and that said Letters Patent is hereby corrected as shown below:

In The Specification

Column 1, line 16, after "entirety." insert -- ¶DESCRIPTION¶ --
Column 5, lines 37-38, replace "Naunyn-Schmeidebery's" with -- Naunyn-Schmeideberg's --
Column 7, line 18, replace "antidepressanats" with -- antidepressants --

In The Claims

Column 10, line 57, in Claim 50, replace "noradrenalin" with -- noradrenaline --

Signed and Sealed this
Twelfth Day of May, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,754,119 B2 | Page 1 of 1 |
| APPLICATION NO. | : 10/565699 | |
| DATED | : June 17, 2014 | |
| INVENTOR(S) | : Scheller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 863 days.

Signed and Sealed this
Eleventh Day of August, 2015

Michelle K. Lee
*Director of the United States Patent and Trademark Office*